US012685843B2

(12) United States Patent
Hochburger

(10) Patent No.: US 12,685,843 B2
(45) Date of Patent: Jul. 21, 2026

(54) AMPLATZ SHEATH AND DILATION SYSTEM

(71) Applicant: UROTECH GMBH, Rohrdorf-Achenmuehle (DE)

(72) Inventor: Tobias Hochburger, Rosenheim (DE)

(73) Assignee: UROTECH GMBH, Rohrdorf-Achenmuehle (DE)

( * ) Notice: Subject to any disclaimer, the term of this patent is extended or adjusted under 35 U.S.C. 154(b) by 667 days.

(21) Appl. No.: 18/026,629

(22) PCT Filed: Sep. 29, 2021

(86) PCT No.: PCT/EP2021/076825
§ 371 (c)(1),
(2) Date: Mar. 16, 2023

(87) PCT Pub. No.: WO2022/069560
PCT Pub. Date: Apr. 7, 2022

(65) Prior Publication Data
US 2023/0330394 A1      Oct. 19, 2023

(30) Foreign Application Priority Data
Oct. 1, 2020    (DE) ..................... 10 2020 125 697.3

(51) Int. Cl.
*A61M 25/00*          (2006.01)
*A61M 25/06*          (2006.01)
(Continued)

(52) U.S. Cl.
CPC .... *A61M 25/0662* (2013.01); *A61M 25/1027* (2013.01); *A61M 29/02* (2013.01);
(Continued)

(58) Field of Classification Search
CPC .. A61M 2025/0008; A61M 2025/0046; A61M 2025/1079; A61M 2025/1081;
(Continued)

(56) References Cited

U.S. PATENT DOCUMENTS 6,796,976 B1      9/2004  Chin et al.
2011/0004057 A1   1/2011  Goldfarb et al.
(Continued)

FOREIGN PATENT DOCUMENTS

CN       101 130 123 A     2/2008
CN       203 802 504 U     9/2014
(Continued)

OTHER PUBLICATIONS

International Search Report in PCT/EP2021/076825, mailed Feb. 11, 2022.
(Continued)

*Primary Examiner* — Deanna K Hall
(74) *Attorney, Agent, or Firm* — Collard & Roe, P.C.

(57)          ABSTRACT
An Amplatz sheath for positioning inside a natural or artificially created bodily cavity in a human or animal has a distal end toward the body and a proximal end away from the body, with at least one lumen being formed between the distal end and the proximal end. At least in a region at the proximal end, the Amplatz sheath is transparent or translucent and, in this region, has at least one marking for determining the position of the Amplatz sheath in relation to a catheter that can be received in the lumen. The Amplatz sheath can be used with a balloon catheter in a dilation system.

13 Claims, 4 Drawing Sheets

Figure 1:
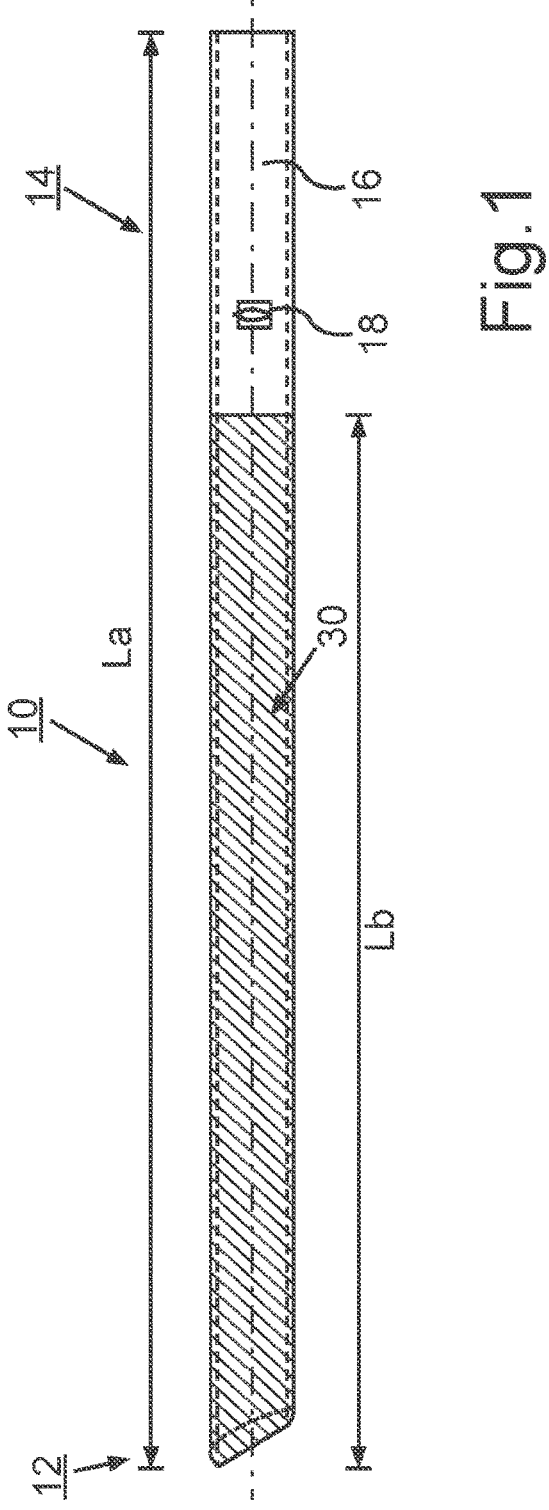

(51) Int. Cl.
   *A61M 25/10*       (2013.01)
   *A61M 29/02*       (2006.01)
(52) U.S. Cl.
   CPC .............. *A61M 2025/0008* (2013.01); *A61M 2025/1079* (2013.01)
(58) Field of Classification Search
   CPC ...... A61M 25/0662; A61M 2025/0681; A61M 2025/0687
   See application file for complete search history.

(56)                References Cited

U.S. PATENT DOCUMENTS

| | | |
|---|---|---|
| 2016/0287055 A1 | 10/2016 | Kesten et al. |
| 2018/0206866 A1* | 7/2018 | Wan ......................... A61B 1/00 |
| 2018/0317995 A1 | 11/2018 | Wilms et al. |

FOREIGN PATENT DOCUMENTS

| | | |
|---|---|---|
| CN | 104 706 458 A | 6/2015 |
| CN | 105 380 716 B | 3/2016 |
| CN | 111 110 333 A | 5/2020 |
| RO | 122 657 B1 | 11/2009 |
| WO | 2016/051421 A1 | 4/2016 |
| WO | 2017/027107 A1 | 2/2017 |

OTHER PUBLICATIONS

Boston Scientific: "Refined Technology. Reliable Performance. NephroMax (TM) High Pressure Nephrostomy Balloon Catheter", Urology and Women's Health, 2012, XP55886523A, total of 4 pages.

English translation of the International Preliminary Report on Patentability and Written Opinion of the International Searching Authority in PCT/EP2021/076825, dated Mar. 28, 2023.

Office Action of Japanese Application No. JP2023-516049, dated Dec. 27, 2024 (With English Translation).

NephroMax "High Pressure Nephrostomy Balloon Catheter", Boston Scientific (2012).

* cited by examiner

AMPLATZ SHEATH AND DILATION SYSTEM

CROSS REFERENCE TO RELATED APPLICATIONS

This application is the National Stage of PCT/EP2021/076825 filed on Sep. 29, 2021, which claims priority under 35 U.S.C. § 119 of German Application No. 10 2020 125 697.3 filed on Oct. 1, 2020, the disclosure of which is incorporated by reference. The international application under PCT article 21(2) was not published in English.

The invention relates to an Amplatz sheath for positioning within a human or animal, natural or artificially created bodily cavity, comprising a distal end toward the body and a proximal end away from the body, wherein at least one lumen is formed between the distal and the proximal end. Furthermore, the invention relates to a dilation system for positioning within a human or animal, natural or artificially created bodily cavity.

Such Amplatz sheaths for positioning within a human or animal, natural or artificially created bodily cavity are known in a great plurality and in particular serve for keeping such bodily cavities open.

Such Amplatz sheaths, which are also known under the terms "Amplatz shaft", "Amplatz sluice" or "working sluice", are for example applied in the percutaneous nephrolithotomy or nephrolitholapaxy, in which an artificially created access to the kidney is kept open by the Amplatz sheath.

However, it is disadvantageous in the known Amplatz sheaths as well as the corresponding dilation systems including such Amplatz sheaths that the Amplatz sheaths can only difficultly and insecurely be placed. Thereby, injuries of the surrounding tissue can occur. Therefore, known Amplatz sheaths and the corresponding dilation systems comprise radiopaque markings in their distal regions, that is toward the body, such that the Amplatz sheaths and the dilation systems, respectively, can be placed within the bodily cavity under x-ray control. However, this requires a high instrumental effort, in addition, the production costs for such Amplatz sheaths and the corresponding dilation systems considerably increase.

It is the object of the present invention to provide an Amplatz sheath and a dilation system of the initially mentioned type, which allow a secure and fast positioning of the Amplatz sheath within a human or animal, natural or artificially created bodily cavity.

This object is solved by an Amplatz sheath with the features of claim 1 and a dilation system with the features of claim 10 or of claim 13. Advantageous configurations with convenient developments of the invention are specified in the respective dependent claims, wherein advantageous configurations of the Amplatz sheath are to be regarded as advantageous configurations of the dilation system and vice versa.

A first aspect of the invention relates to an Amplatz sheath for positioning within a human or animal, natural or artificially created bodily cavity, comprising a distal end toward the body and a proximal end away from the body, wherein at least one lumen is formed between the distal and the proximal end. Therein, it is known to the expert that the lumen is continuously formed between the distal and the proximal end. Furthermore, the Amplatz sheath is transparently or translucently formed at least in a region of its proximal end. In addition, at least one marking for position determination of the Amplatz sheath in relation to a catheter receivable in the lumen is formed in this region. By the transparent or translucent formation of the proximal end of the Amplatz sheath as well as the marking attached there, the relative position of the Amplatz sheath in relation to a catheter guided in the lumen can be securely and simply determined. Since the marking is located at the proximal end of the Amplatz sheath, it still protrudes from the bodily cavity and is optically well visible. Laborious positionings of the Amplatz sheath under x-ray control are thereby avoided. In addition, the marking can be applied to the Amplatz sheath in simple manner. For example, it can be effected by means of a printing method, a gravure method and/or by adhering on a surface of the Amplatz sheath in the region of the proximal end. The marking can be formed on the outer and/or inner surface of the Amplatz sheath.

In particular, tubular supply systems such as for example balloon catheters, are understood by the term "catheter". If the catheter is a balloon catheter, thus, the marking can be arranged on the Amplatz sheath such that it can be aligned with a proximal end of a balloon of the balloon catheter. Therein, the proximal end of the balloon of the balloon catheter serves as a position marking, which reflects the position of the Amplatz sheath in the bodily cavity. Therein, it can in particular be previously defined via a corresponding length of the Amplatz sheath, how far the Amplatz sheath, in particular the distal end thereof, is advanced on the catheter towards the bodily cavity when the marking is for example aligned with the proximal end of the balloon of the balloon catheter. Therein, it is crucial that the length of the Amplatz sheath is selected such that upon overlap of the marking with for example the proximal end of the balloon of the balloon catheter or also another marking of a catheter, which is guided within the lumen of the Amplatz sheath, the distal end of the Amplatz sheath does not protrude beyond the distal end of the balloon catheter or of the catheter. The distal end of the Amplatz sheath can also be matched with the distal end of the balloon catheter or of the catheter. Thereby, according to the invention, it is reliably prevented that a damage of tissue by too far advance of the Amplatz sheath in the surrounding, in particular the distal regions of the bodily cavity can occur.

However, further Amplatz sheaths are also understood by the term "catheter", wherein these Amplatz sheaths have to be formed such that they can be arranged and displaced within the lumen of the Amplatz sheath according to the invention. This means that such Amplatz sheaths have to have a lower diameter than the Amplatz sheath according to the invention. For example, a bodily cavity can be dilated to a required diameter in that an Amplatz sheath with a small diameter is first introduced. Subsequently, the Amplatz sheath according to the invention can for example be shifted over the first introduced sheath.

In advantageous configurations of the Amplatz sheath according to the invention, it is composed of a biotolerable and/or biocompatible plastic. In particular, the Amplatz sheath can be at least partially composed of polyvinylpyrrolidone (PVP), polytetrafluoroethylene (PTFE), phosphorylcholine or polypropylene (PP).

In addition, there is the possibility that the distal end of the Amplatz sheath is chamfered on one side or conically formed. Thereby, the Amplatz sheath can be simpler introduced into the bodily cavity such that injuries of the surrounding tissue can be prevented or at least minimized. The required force effort in introducing the Amplatz sheath into the bodily cavity also decreases In further advantageous configurations of the Amplatz sheath according to the invention, it comprises a hydrophilic coating on its outer and/or inner surface at least in the region of the distal end. Hydrophilic coatings ensure that a uniform liquid film forms on the corresponding surface of the Amplatz sheath, which acts like a lubricating film between the outer surface of the Amplatz sheath and the surrounding tissue and/or the inner surface of the Amplatz sheath and the catheter guided in the lumen. This liquid film reduces the friction to high extent and thus protects the tissue from injuries on the one hand and the catheter guided in the Amplatz sheath from damages on the other hand. In addition, the required force for advancing the Amplatz sheath in the bodily cavity as well as the force effort for shifting the Amplatz sheath for example onto an inflated balloon of a balloon catheter decreases. Hereby too, traumatizations of the surrounding tissue as well as damages of the catheter or balloon catheter can be prevented.

Therein, the coating can be formed over 25 to 90% of the length of the Amplatz sheath starting from the distal end of the Amplatz sheath. In that the coating, in particular on the surface of the Amplatz sheath, does not encompass the proximal end of the Amplatz sheath, the user can grip the Amplatz sheath without the danger of slipping off existing. In the following table 1, lengths are exemplarily indicated, wherein La presents the overall length of the Amplatz sheath, measured from a distal tip and the proximal end of the Amplatz sheath, and Lb presents the approximate length or length extension Lb of the coating, measured from the distal tip of the Amplatz sheath up to a proximal end of the coating on the outer and/or inner surface of the Amplatz sheath.

TABLE 1

| La (in mm) | Lb (in mm) |
|---|---|
| 165 | 125 ± 5 |
| 165 | 125 ± 5 |
| 194 | 150 ± 5 |

Therein, in particular percentage values of 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90% are to be understood by a percent range of 25 to 90%, wherein percentage values between 50 and 85% have proven particularly advantageous for most of the applications. Intermediate values not explicitly indicated above are also possible.

Furthermore, there is the possibility that the hydrophilic coating is selected from the group consisting of a hydrophilic polymer or of a combination of multiple hydrophilic polymers. For example, polyvinylpyrrolidone (PVP) can be used for the hydrophilic coating. The above described specific coating of the Amplatz sheath has an own inventive content, which also includes Amplatz sheaths without the mentioned marking.

A second aspect of the present invention relates to a dilation system for positioning within a human or animal, natural or artificially created bodily cavity, comprising an Amplatz sheath according to the above described first inventive aspect and a balloon catheter. Therein, the balloon catheter comprises at least one balloon with a distal end toward the body and a proximal end away from the body. In addition, it is formed such that it can be arranged in the lumen of the Amplatz sheath.

According to the invention, for position determination of the Amplatz sheath within the bodily cavity, the marking arranged in the region of the proximal end of the Amplatz sheath can be aligned with the proximal end of the balloon or a further marking formed in this region by corresponding displacement of the Amplatz sheath in relation to the balloon catheter. Since the Amplatz sheath is transparently or translucently formed, an optical indication is given to the user when the desired positioning in the bodily cavity is reached. Upon positioning of the Amplatz sheath, it usually is not to protrude beyond the distal end of the balloon catheter. Therefore, the length of the Amplatz sheath can be selected such that upon overlap of the proximal end of the balloon or of the further marking attached in this region with the marking of the Amplatz sheath, the distal end of the Amplatz sheath does not protrude beyond the distal end of the balloon and/or of the balloon catheter. The length can also be selected such that the distal end of the Amplatz sheath is matched with the distal end of the balloon and/or of the balloon catheter after desired positioning. Thereby, it is ensured in simple manner that an unintended injury of tissue within the bodily cavity, which surrounds the dilation system, does not occur. In particular the regions distal to the dilation system are protected from too far advance of the Amplatz sheath and the possible injuries associated therewith.

Further features and the advantages thereof of the dilation system according to the invention can be taken from the description of the first inventive aspect.

A third aspect of the present invention relates to a dilation system for positioning an Amplatz sheath within a human or animal, natural or artificially created bodily cavity, comprising an Amplatz sheath and a balloon catheter, wherein the balloon catheter comprises at least one balloon with a distal end toward the body and a proximal end away from the body and is formed such that it can be arranged in the lumen of the Amplatz sheath. For position determination of the Amplatz sheath within the bodily cavity, according to the invention, a termination edge of a proximal end of the Amplatz sheath away from the body or at least one marking arranged in the region of the proximal end of the Amplatz sheath away from the body can therein be aligned with at least one marking arranged in the region of the proximal end of the balloon catheter away from the body by corresponding displacement of the Amplatz sheath in relation to the balloon catheter. Thereby, on the one hand, there is the possibility that even with non-transparently or non-translucently formed Amplatz sheaths, an optical indication is given to the user when the desired positioning in the bodily cavity is reached. Upon positioning of the Amplatz sheath, it usually is not to protrude beyond the distal end of the balloon catheter. Therein, the length of the Amplatz sheath can be selected such that upon overlap of the proximal termination edge of the Amplatz sheath with the proximal marking of the balloon catheter, a distal end of the Amplatz sheath toward the body does not protrude beyond the distal end of the balloon and/or of the balloon catheter. However, there is also the possibility that the length of the Amplatz sheath is selected such that with an overlap of the proximal termination edge of the Amplatz sheath with the proximal marking of the balloon catheter, the distal end of the Amplatz sheath toward the body is matched or aligned with the distal end of the balloon and/or of the balloon catheter. On the other hand, the same applies to Amplatz sheaths transparently or translucently formed at least in the proximal region away from the body. However, here is additionally the possibility that with an overlap of the proximal marking of the Amplatz sheath with the proximal marking of the balloon catheter, the distal end of the Amplatz sheath toward the body does not protrude beyond the distal end of the balloon and/or of the balloon catheter or is aligned or matched with it by corresponding displacement of the Amplatz sheath in relation to the balloon catheter. Hereby too, an optical indication of the position of the Amplatz sheath in the bodily cavity is given to the user. Thereby, it is ensured in simple manner that an unintended injury of tissue within the bodily cavity, which surrounds the dilation system, does not occur. In particular the regions distal to the dilation system are protected from too far advance of the Amplatz sheath and the possible injuries associated therewith.

Figure 2:
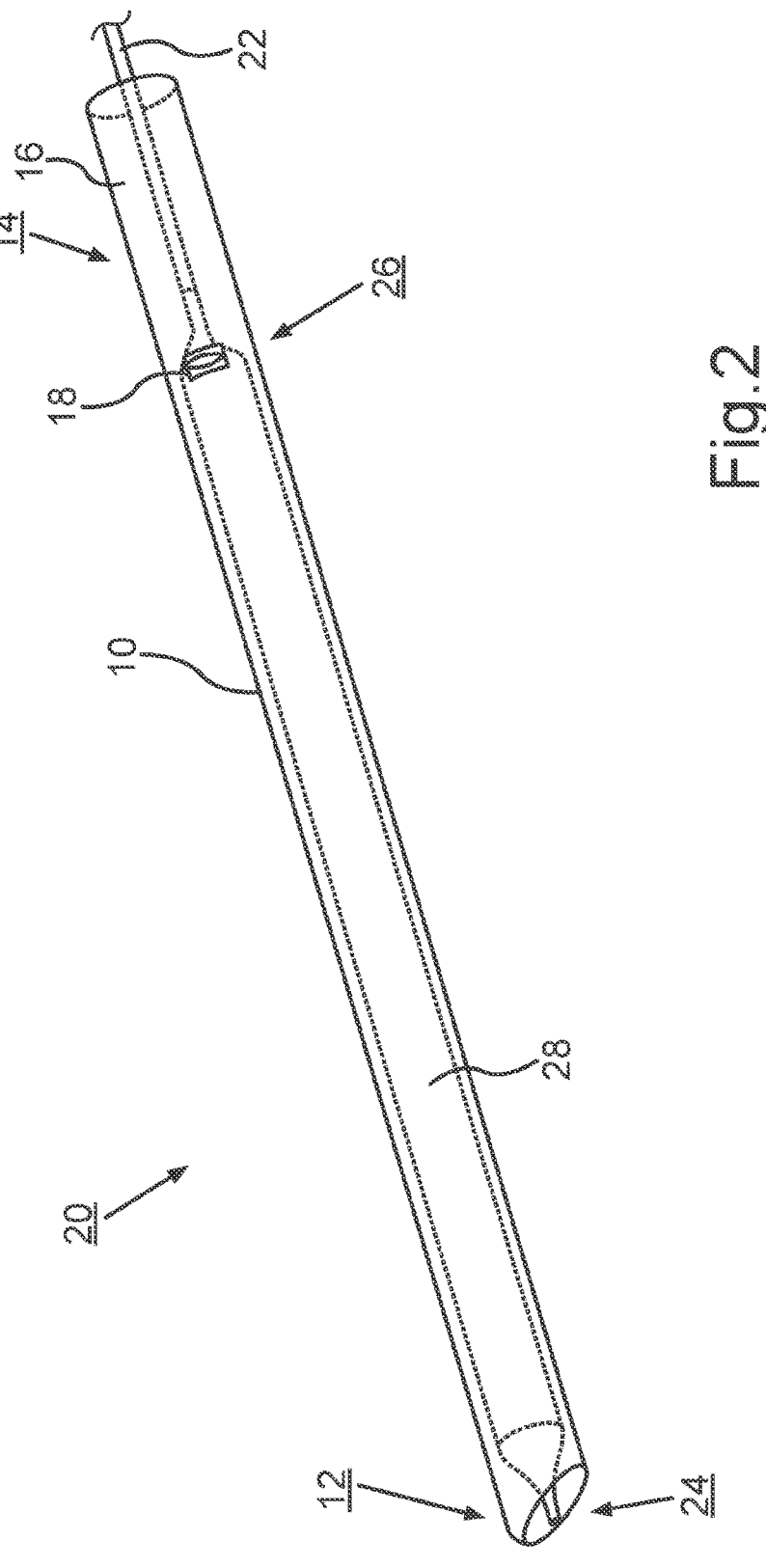
Figure 3:
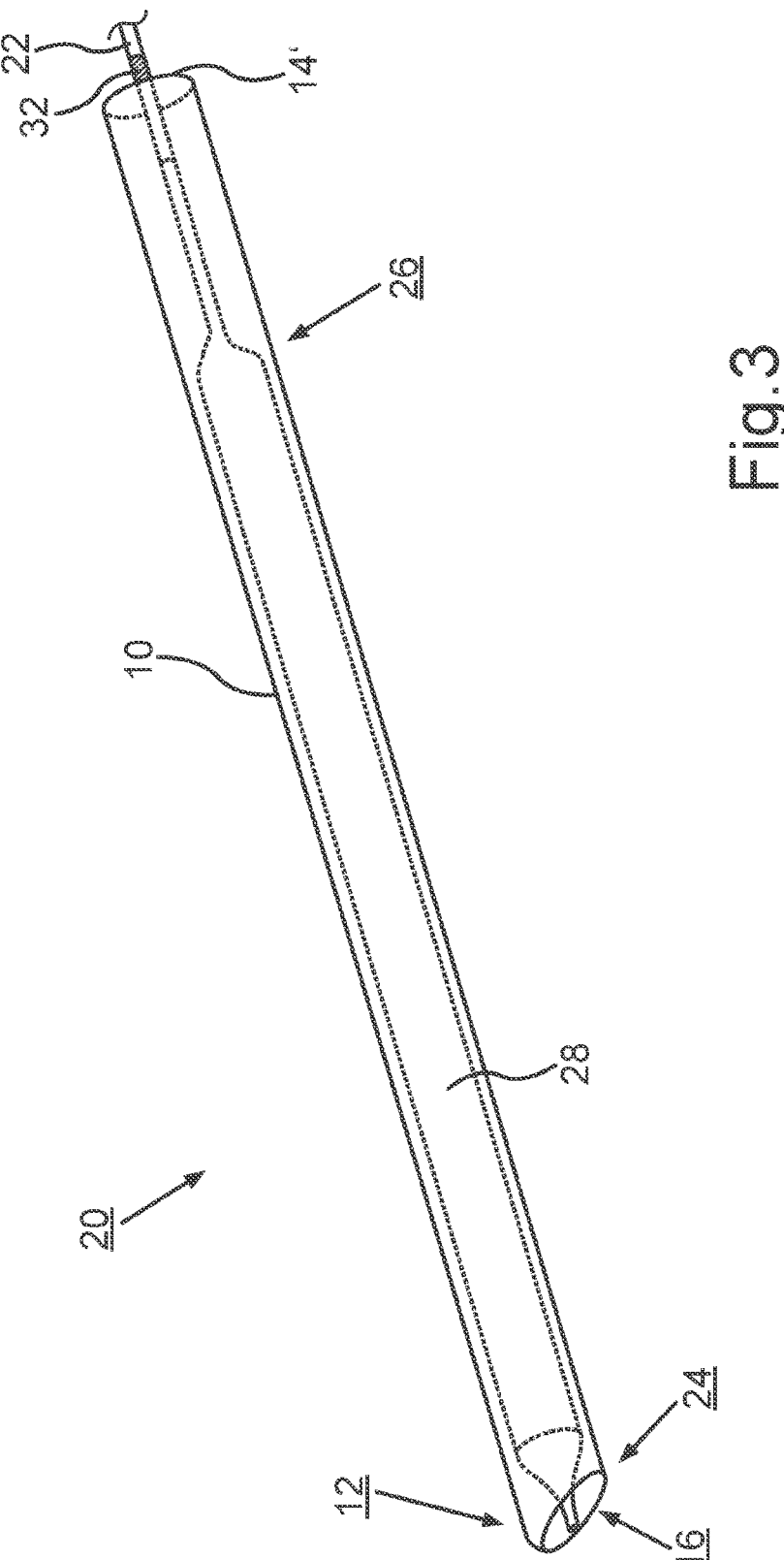
Figure 4:
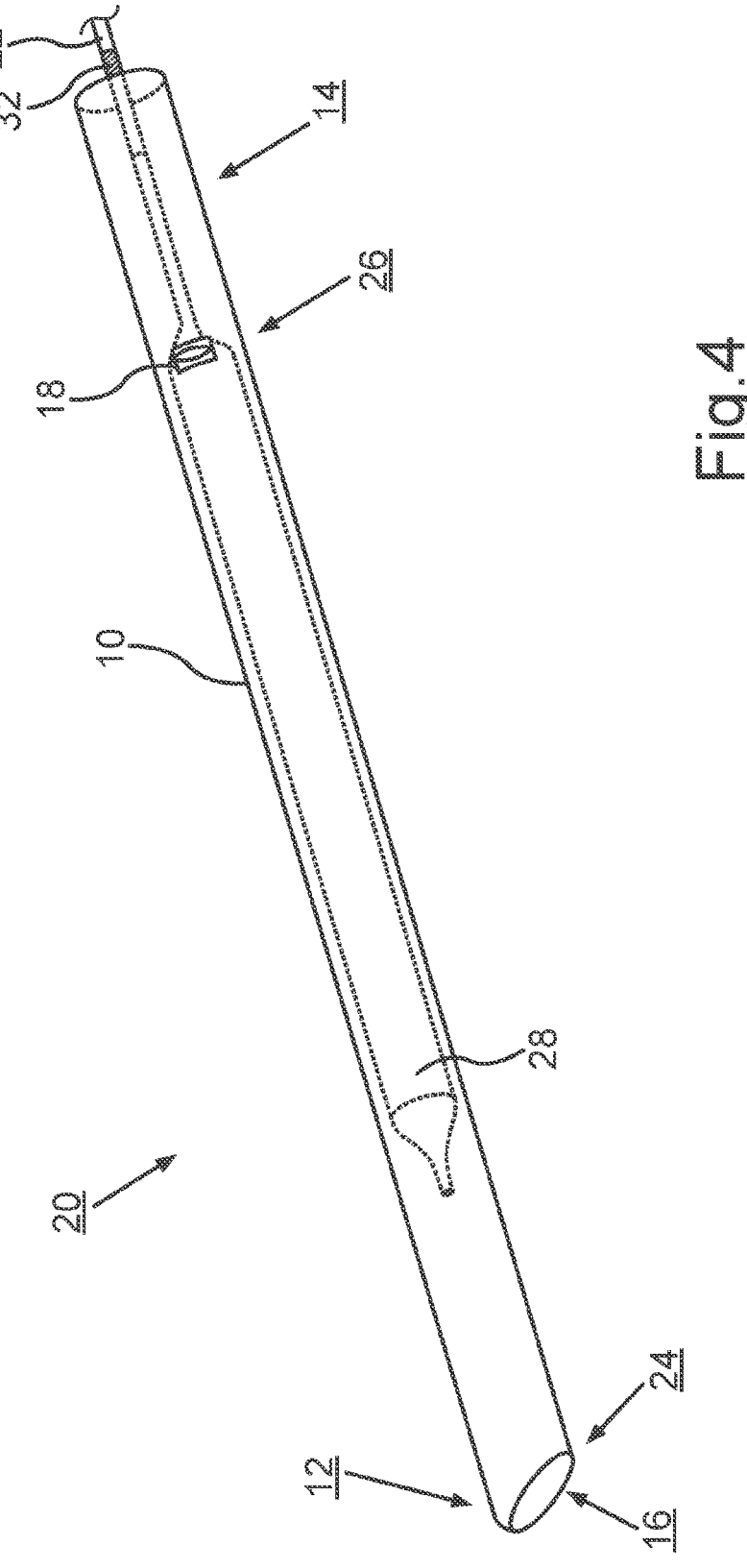

In addition, further features of the invention are apparent from the claims, the embodiment as well as based on the drawing. The features and feature combinations mentioned above in the description as well as the features and feature combinations mentioned below in the embodiments are usable not only in the respectively specified combination, but also in other combinations without departing from the scope of the invention. There shows:

FIG. 1 a schematic representation of an Amplatz sheath according to the invention;

FIG. 2 a schematic representation of a dilation system according to the invention according to a first embodiment;

FIG. 3 a schematic representation of a dilation system according to the invention according to a second embodiment; and FIG. 4 a schematic representation of a dilation system according to the invention according to a third embodiment.

FIG. 1 shows a schematic representation of an Amplatz sheath 10. Usually, the Amplatz sheath 10 serves for positioning within a human or animal, natural or artificially created bodily cavity and is to keep it open or create and provide a corresponding accessibility. The Amplatz sheath 10 includes a distal end 12 toward the body and a proximal end 14 away from the body, wherein a lumen 16 is formed between the distal and the proximal end 12, 14. However, it is also conceivable that further lumens are formed. One recognizes that the Amplatz sheath 10 shown in the illustrated embodiment is overall transparently formed. However, it would basically be sufficient if the Amplatz sheath 10 is transparently or translucently formed only in the region of the proximal end 14. Furthermore, one recognizes that it comprises a marking 18 in the region of the proximal end 14 for relative position determination of the Amplatz sheath 10 in relation to a catheter 22 (compare FIG. 2) receivable in the lumen 16. In the illustrated embodiment, the marking 18 is imprinted. However, there is also the possibility that corresponding markings are engraved or adhered.

A length La of the Amplatz sheath 10 is selected such that upon positioning of the Amplatz sheath 10 within the bodily cavity, at least the proximal region of the Amplatz sheath 10, which includes the marking 18, protrudes from the bodily cavity. Thereby, it is ensured that the marking 18 is visible on the one hand and the Amplatz sheath 10 can be readily gripped and moved at the proximal end 14 on the other hand.

Furthermore, one recognizes that the Amplatz sheath 10 according to the shown embodiment comprises a hydrophilic coating 30 on its outer and inner surface. One recognizes that the coating 30 extends over ca. 75% of the length of the Amplatz sheath 10 in proximal direction starting from the distal end 12. The region at the proximal end 14 of the Amplatz sheath 10 is not coated such that this region can be well gripped. Concrete examples for the length ratio of the Amplatz sheath La to the length of the coating Lb can be taken from table 1. Usually, the hydrophilic coating is composed of a hydrophilic polymer or of a combination of multiple hydrophilic polymers as well as further possible additives.

Furthermore, one recognizes that the distal end 12 of the Amplatz sheath 10 is formed chamfered on one side. Such a configuration of the distal end 12 facilitates the advance into the bodily cavity or the advance onto an inflated balloon of a balloon catheter.

FIG. 2 shows a schematic representation of a dilation system 20 according to a first embodiment. The dilation system 20 serves for positioning an Amplatz sheath 10 within a human and animal, natural or artificially created bodily cavity. Therein, the dilation system 20 includes the Amplatz sheath 10 as it has been described in FIG. 1. Furthermore, the dilation system 20 includes a balloon catheter 22 with a balloon 28. The balloon 28 comprises a distal end 24 toward the body and a proximal end 26 away from the body. In addition, the balloon catheter 22 is formed such that it can be positioned, arranged and displaced in the lumen 16 of the Amplatz sheath 10. In the illustrated embodiment, the balloon 28 is completely arranged within the lumen 16 of the Amplatz sheath 10. In use, the balloon catheter 22 is usually shifted into the bodily cavity in distal direction. When the balloon 28 has reached the location to be dilated within the bodily cavity, the balloon 28 is dilated up to the predetermined size via corresponding liquid conducting lines within the balloon catheter 22. After the dilation of the body constriction within the bodily cavity has been effected, the Amplatz sheath 10 is introduced into the bodily cavity also in distal direction. For a position determination of the Amplatz sheath 10 within the bodily cavity, the marking 18 has to be aligned with the proximal end 26 of the balloon 28 by corresponding displacement of the Amplatz sheath 10 in relation to the balloon catheter 22. In this position, it is ensured that the distal end 12 of the Amplatz sheath 10 does not protrude beyond the distal end 24 of the balloon 28 or of the balloon catheter 22. In this position, the distal end 12 is usually matched with the distal end 24 of the balloon 28. After retracting the balloon catheter 22 in proximal direction, the Amplatz sheath 10 remains in the predefined position within the bodily cavity and thus keeps a corresponding accessibility via the lumen 16 free.

FIG. 3 shows a schematic representation of a dilation system 20 according to a second embodiment. The basic construction of the dilation system 20 illustrated here corresponds to the construction of the dilation system shown in FIG. 2. Therein, the dilation system 20 again includes the Amplatz sheath 10 and a balloon catheter 22, wherein the balloon catheter 22 comprises a balloon 28 with a distal end 24 toward the body and a proximal end 26 away from the body. In addition, it is formed such that it can be arranged in the lumen 16 of the Amplatz sheath 10. One recognizes that in contrast to the first embodiment of the dilation system 20 illustrated in FIG. 2, the balloon catheter 22 of the dilation system 20 according to the second embodiment comprises a marking 32 at its proximal section away from the body. This marking 32 serves for position determination of the Amplatz sheath 10 within the bodily cavity. Hereto, a termination edge 14' of the proximal end 14 of the Amplatz sheath away from the body is aligned with the marking 32 by corresponding displacement of the Amplatz sheath 10 in relation to the balloon catheter 22. Therein, the length of the Amplatz sheath 10 is selected such that upon overlap of the proximal termination edge 14' with the proximal marking 32 of the balloon catheter 22, the distal end 12 of the Amplatz sheath 10 toward the body does not protrude beyond the distal end 24 of the balloon 28 and/or of the balloon catheter 22. However, there is also the possibility that the length of the Amplatz sheath 10 is selected such that upon overlap of the proximal termination edge 14' with the proximal marking 32 of the balloon catheter 22, the distal end 12 of the Amplatz sheath 10 is matched or aligned with the distal end 24 of the balloon 28 and/or of the balloon catheter 22 (schematically illustrated in FIG. 3). Thereby, it is ensured in both cases that the distal end 12 of the Amplatz sheath 10 does not protrude beyond the distal end 24 of the balloon 28 or of the balloon catheter 22.

FIG. 4 shows a schematic representation of a dilation system 20 according to a third embodiment. The basic construction of the dilation system 20 illustrated here corresponds to the construction of the dilation systems shown in FIGS. 2 and 3. In addition to the marking 18, which is arranged in the region of the proximal end 14 of the Amplatz sheath 10 away from the body, the proximal section of the balloon catheter 22 away from the body comprises the further marking 32. Both markings 18, 32 serve for position determination of the Amplatz sheath 10 within the bodily cavity. Hereto, the markings 18, 32 are aligned by corresponding displacement of the Amplatz sheath 10 in relation to the balloon catheter 22. Therein, the length of the Amplatz sheath 10 is selected such that upon a corresponding overlap of the two markings 18, 32, the distal end 12 of the Amplatz sheath 10 toward the body does not protrude beyond the distal end 24 of the balloon 28 and/or of the balloon catheter 22. However, there is also the possibility that the length of the Amplatz sheath 10 is selected such that upon overlap of the two markings 18, 32, the distal end 12 of the Amplatz sheath 10 is matched or aligned with the distal end 24 of the balloon 28 and/or of the balloon catheter 22. Thereby, it is ensured in both cases that the distal end 12 of the Amplatz sheath 10 does not protrude beyond the distal end 24 of the balloon 28 or of the balloon catheter 22. In FIG. 4, a situation is illustrated, in which the marking 32 is not yet aligned with the marking 18.

The invention claimed is:

1. A dilation system (20) for positioning an Amplatz sheath (10) within a natural or artificially created bodily cavity of a body of a human or animal, comprising an Amplatz sheath (10) and a balloon catheter (22), wherein the Amplatz sheath (10) comprises a distal end (12) toward the body and a proximal end (14) away from the body, wherein at least one lumen (16) is formed between the distal and the proximal end (12, 14), wherein the Amplatz sheath (10) is transparently or translucently formed at least in a region at the proximal end (14) and comprises at least one marking (18) in this region for position determination of the Amplatz sheath (10) in relation to the balloon catheter (22) receivable in the lumen (18), wherein the balloon catheter (22) comprises at least one balloon (28) with a distal end (24) toward the body and a proximal end (26) away from the body and is formed such that it the balloon catheter can be arranged in the lumen (16) of the Amplatz sheath (10), wherein for a relative position determination of the Amplatz sheath (10) in relation to the balloon catheter (22) guided in the lumen (16) within the bodily cavity, the marking (18) can be aligned with the proximal end (26) of the balloon (28) or a further marking formed in a region of the proximal end (26) of the balloon (28), and wherein a length of the Amplatz sheath (10) is selected such that after positioning of the Amplatz sheath (10) in the bodily cavity, the region of the proximal end (14) comprising the marking (18) protrudes from the bodily cavity.

2. The dilation system (20) according to claim 1, wherein the Amplatz sheath (10) is composed of a biotolerable and/or biocompatible plastic.

3. The dilation system (20) according to claim 1, wherein the Amplatz sheath (10) is at least partially composed of polyvinylpyrrolidone (PVP), polytetrafluoroethylene (PTFE), phosphorylcholine or polypropylene (PP).

4. The dilation system (20) according to claim 1, wherein the marking (18) is applied to a surface of the Amplatz sheath (10) by means of a printing method, a gravure method and/or by adhering.

5. The dilation system (20) according to claim 1, wherein the Amplatz sheath (10) comprises a hydrophilic coating (30) on an outer and/or inner surface at least in a region of the distal end (12).

6. The dilation system (20) according to claim 5, wherein the coating (30) is formed over 25-90% of the length of the Amplatz sheath (10) starting from the distal end (12).

7. The dilation system according to claim 5, wherein the hydrophilic coating (30) is selected from the group consisting of a hydrophilic polymer and a combination of multiple hydrophilic polymers.

8. The dilation system according to claim 1, wherein the distal end (12) of the Amplatz sheath (12) is chamfered on one side or conically formed.

9. The dilation system (20) according to claim 1, wherein the length of the Amplatz sheath (10) is selected such that upon overlap of the proximal end (26) of the balloon (28) or the further marking with the marking (18) of the Amplatz sheath (10), the distal end (12) of the Amplatz sheath (10) does not protrude beyond the distal end (24) of the balloon (28) and/or of the balloon catheter (22).

10. The dilation system (20) according to claim 1, wherein the length of the Amplatz sheath (10) is selected such that upon overlap of the proximal end (26) of the balloon (28) or of the further marking with the marking (18) of the Amplatz sheath (10), the distal end (12) of the Amplatz sheath (10) is matched with the distal end (24) of the balloon (28) and/or of the balloon catheter (22).

11. A dilation system (20) for positioning an Amplatz sheath (10) within a natural or artificially created bodily cavity of a body of a human or animal, comprising an Amplatz sheath (10) and a balloon catheter (22), wherein the Amplatz sheath (10) comprises a distal end (12) toward the body and a proximal end (14) away from the body, wherein at least one lumen (16) is formed between the distal and the proximal end (12, 14), wherein the Amplatz sheath (10) is transparently or translucently formed at least in a region at the proximal end (14) and comprises at least one marking (18) in this region for position determination of the Amplatz sheath (10) in relation to the balloon catheter (22) receivable in the lumen (16), wherein the balloon catheter (22) comprises at least one balloon (28) with a distal end (24) toward the body and a proximal end (26) away from the body and is formed such that the balloon catheter can be arranged in the lumen (16) of the Amplatz sheath (10), wherein for a relative position determination of the Amplatz sheath (10) in relation to the balloon catheter (22) guided in the lumen (16) within the bodily cavity, a termination edge (14') of a proximal end (14) of the Amplatz sheath (10) away from the body or the at least one marking (18) arranged in the region of the proximal end (14) of the Amplatz sheath (10) away from the body can be aligned with at least one marking (32) arranged in the region of the proximal end of the balloon catheter (22) away from the body, and wherein a length of the Amplatz sheath (10) is selected such that after positioning of the Amplatz sheath (10) in the bodily cavity, the region of the proximal end (14) comprising the marking (18) protrudes from the bodily cavity.

12. The dilation system (20) according to claim 11, wherein the length of the Amplatz sheath (10) is selected such that upon overlap of the proximal termination edge (14') of the Amplatz sheath (10) or upon overlap of the proximal marking (18) of the Amplatz sheath (10) with the proximal marking (32) of the balloon catheter (22), a distal end (12) of the Amplatz sheath (10) toward the body does not protrude beyond the distal end (24) of the balloon (28) and/or of the balloon catheter (22).

13. The dilation system (20) according to claim 11, wherein the length of the Amplatz sheath (10) is selected such that upon overlap of the proximal termination edge (14') of the Amplatz sheath (10) or upon overlap of the proximal marking (18) of the Amplatz sheath (10) with the proximal marking (32) of the balloon catheter (22), a distal end (12) of the Amplatz sheath (10) toward the body is matched with the distal end (24) of the balloon (28) and/or of the balloon catheter (22).

\* \* \* \* \*